United States Patent
Davies

(10) Patent No.: US 12,186,130 B2
(45) Date of Patent: Jan. 7, 2025

(54) ANNULAR INTEGRATED CIRCUIT CONTROLLER FOR INTRALUMINAL ULTRASOUND IMAGING DEVICE

(71) Applicant: KONINKLIJKE PHILIPS N.V., Eindhoven (NL)

(72) Inventor: Stephen Charles Davies, El Dorado Hills, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 592 days.

(21) Appl. No.: 16/495,593

(22) PCT Filed: Apr. 2, 2018

(86) PCT No.: PCT/EP2018/058378
§ 371 (c)(1),
(2) Date: Sep. 19, 2019

(87) PCT Pub. No.: WO2018/178382
PCT Pub. Date: Oct. 4, 2018

(65) Prior Publication Data
US 2020/0008781 A1 Jan. 9, 2020

Related U.S. Application Data

(60) Provisional application No. 62/479,412, filed on Mar. 31, 2017.

(51) Int. Cl.
*A61B 8/00* (2006.01)
*A61B 8/12* (2006.01)
(Continued)

(52) U.S. Cl.
CPC ............... *A61B 8/445* (2013.01); *A61B 8/12* (2013.01); *A61B 8/4494* (2013.01); *A61B 8/54* (2013.01);
(Continued)

(58) Field of Classification Search
CPC ......... A61B 8/445; A61B 8/12; A61B 8/4494; A61B 8/54; B06B 1/0207; B06B 1/0625; B06B 1/0633
See application file for complete search history.

(56) References Cited

U.S. PATENT DOCUMENTS 5,368,037 A * 11/1994 Eberle ............... A61B 8/12
600/463
7,846,101 B2  12/2010 Eberle
(Continued)

FOREIGN PATENT DOCUMENTS

WO    2017001525 A1    1/2017

OTHER PUBLICATIONS

International Search Report & Written Opinion for PCT/EP2018/058378, dated Jul. 2, 2018.
(Continued)

*Primary Examiner* — Joel Lamprecht
*Assistant Examiner* — James F McDonald, III

(57) ABSTRACT

An intraluminal imaging device is provided. In one embodiment, the imaging device includes a flexible elongate member that may be inserted into a body lumen within a patient. The flexible elongate member may define a longitudinal axis. The imaging device also has an imaging assembly that is disposed at a distal portion of the flexible elongate member. The imaging assembly may have a plurality of ultrasound transducer elements disposed around the longitudinal axis. The imaging assembly further includes a first integrated circuit controller in communication with the
(Continued)

plurality of ultrasound transducer elements. The first integrated circuit controller may be annularly shaped. In some embodiments, the imaging assembly may include a second integrated circuit controller in communication with the ultrasound transducer elements and the first integrated circuit controller. The second integrated circuit controller may be annularly shaped.

23 Claims, 12 Drawing Sheets

(51) Int. Cl.
    *B06B 1/02*     (2006.01)
    *B06B 1/06*     (2006.01)
(52) U.S. Cl.
    CPC .......... *B06B 1/0207* (2013.01); *B06B 1/0625* (2013.01); *B06B 1/0633* (2013.01)

(56) References Cited

U.S. PATENT DOCUMENTS

| | | | |
|---|---|---|---|
| 2004/0254442 A1* | 12/2004 | Williams | A61B 5/6852 600/407 |
| 2008/0200814 A1* | 8/2008 | Imahashi | B06B 1/0633 600/463 |
| 2016/0029999 A1* | 2/2016 | Corl | A61B 8/4494 600/463 |
| 2017/0303893 A1* | 10/2017 | Sato | B06B 1/0625 |

OTHER PUBLICATIONS

Stoute, Ronald et al "Optical Data Link assembly for 360 [mu]m diamter IVUS on Guidewire Imaging Devices", IEEE Sensors 2014 Proceedings, pp. 217-220.

* cited by examiner

ANNULAR INTEGRATED CIRCUIT CONTROLLER FOR INTRALUMINAL ULTRASOUND IMAGING DEVICE

RELATED APPLICATION

This application claims the benefit of and priority to U.S. Provisional Application No. 62/479,412, filed Mar. 31, 2017, which is incorporated by reference in its entirety.

TECHNICAL FIELD

The present disclosure relates generally to devices for imaging within a body of a subject. In particular, an annularly-shaped integrated circuit controller for an intraluminal ultrasound imaging device is provided.

BACKGROUND

Intravascular imaging is widely used in interventional cardiology as a diagnostic tool for assessing a diseased vessel, such as an artery within the human body, to determine the need for treatment. Intravascular imaging can further be used to guide the intervention and/or to assess the effectiveness of the intervention. An intravascular imaging device including one or more ultrasound transducers is passed into the vessel and is guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an intravascular imaging system. The imaging system processes the received ultrasound echoes to produce a cross-sectional image of the vessel where the device is placed.

Solid-state (also known as synthetic-aperture) intravascular imaging catheters are one of the two types of intravascular imaging devices commonly used today, the other type being the rotational intravascular imaging catheter. Solid-state intravascular imaging catheters carry an imaging device that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state intravascular imaging system can synthesize the effect of a mechanically scanned ultrasound transducer but without moving parts (hence the solid-state designation). Since there is no rotating mechanical element, the transducer array can be placed in direct contact with the blood and close to the vessel tissue with minimal risk of vessel trauma. Furthermore, because there is no rotating element, the electrical interface is simplified. The solid-state scanner can be wired directly to the imaging system with a simple electrical cable and a detachable electrical connector, unlike the complex rotating electrical interface used for a rotational intravascular imaging device.

Manufacturing an intraluminal imaging device that can efficiently traverse physiology within the human body is challenging. For example, traditional integrated circuit controller chips are rectangular and are positioned longitudinally along the length of the imaging device. This contributes to the length of the imaging device that is stiff and unable to bend while moving through tortuous anatomy. Traditional manufacturing methods, such as dicing, limit the shape of integrated circuit controllers.

SUMMARY

Embodiments of the present disclosure provide an improved intraluminal imaging device for generating images of a lumen within the body of a patient, such as a blood vessel. An ultrasound imaging assembly includes one or more annularly-shaped integrated circuit controllers that control a plurality of transducer elements to emit ultrasonic energy and receive reflected ultrasound echoes. The annularly-shaped integrated circuit controllers extend a smaller distance longitudinally along the length of the imaging device, compared to traditional rectangular controllers. Thus, implementing the annularly-shaped integrated circuit controllers advantageously reduces the stiff length of the imaging assembly and improves the ability of the imaging device to easily traverse tortuous anatomy within a patient.

Embodiments of the present disclosure provide an intraluminal imaging device that may include a flexible elongate member that may be inserted into a body lumen within a patient. The flexible elongate member may define a longitudinal axis. The intraluminal imaging device also includes an imaging assembly that may disposed at a distal portion of the flexible elongate member. The imaging assembly may include a plurality of ultrasound transducer elements that are disposed around the longitudinal axis. The imaging assembly also includes a first integrated circuit controller in communication with the plurality of ultrasound transducer elements. The first integrated circuit controller may be annularly shaped.

In some embodiment, the intraluminal imaging device further includes a second integrated circuit controller in communication with the ultrasound transducer elements and the first integrated circuit controller such that the second integrated circuit controller is annularly shaped. In some embodiment, the imaging assembly further includes a flexible substrate such that the plurality of ultrasound transducer elements is formed on the flexible substrate. The flexible substrate may extend longitudinally between the first and second integrated circuit controllers.

In some examples, the first integrated circuit controller may be positioned proximally of the plurality of ultrasound transducer elements and the second integrated circuit controller may be positioned distally of the plurality of ultrasound transducer elements. In some examples, the flexible elongate member may have an inner member extending through an inner diameter of the first and second integrated circuit controllers. Also, an acoustic backing material may be disposed in a space defined by the inner member, the first and second integrated circuit controllers, and the plurality of ultrasound transducer elements.

In some embodiments, the flexible elongate member may have an outer member and an inner member. The inner member may have a conductive trace such that the first and second integrated circuit controllers are in electrical communication via the conductive trace of the inner member. In some embodiments, the first and second integrated circuit controllers may include an inner diameter and an outer diameter such that the inner member of the flexible elongate member extends through the inner diameters of the first and second integrated circuit controllers.

In some examples, positioning the first integrated circuit controller may include extending an inner member of the flexible elongate member through an inner diameter of the first integrated circuit controller and positioning the second integrated circuit controller may include extending the inner member of the flexible elongate member through an inner diameter of the second integrated circuit controller. In some examples, the inner diameters of the first and second integrated circuit controllers include an inner bond pad in contact with the conductive trace of the inner member. In some examples, the outer diameter of the first integrated circuit controller includes a plurality of outer bond pads in contact with the plurality of ultrasound transducer elements.

In some examples, a quantity of the plurality of outer bond pads may be equal to a quantity of the plurality of ultrasound transducer elements. In some embodiments, the first integrated circuit controller have a plurality of back bond pads coupled to a plurality of conductors extending along a length of the flexible elongate member. In some examples, a length of the first integrated circuit controller in a longitudinal direction is 3 mm or less.

In some embodiments, a method of assembling of an intraluminal imaging device incudes positioning a first integrated circuit controller at a distal portion of a flexible elongate member. The flexible elongate member may be inserted into a body lumen within a patient. The first integrated circuit controller may be annularly shaped. The method also includes positioning a plurality of ultrasound transducer elements around a longitudinal axis of the flexible elongate member at the distal portion. The method further includes establishing electrical communication between the first integrated circuit controller and the plurality of ultrasound transducer elements.

In some embodiments, the method includes positioning a second integrated circuit controller at the distal portion of the flexible elongate member such that the second integrated circuit controller may be annularly shaped. In some embodiments, the method includes etching the first integrated circuit controller into the annular shape.

In some embodiments, the method includes establishing electrical communication between the first and second integrated circuit controllers. In some examples, establishing electrical communication may include contacting an inner bond pad disposed on inner diameters of the first and second integrated circuit controllers to a conductive trace disposed on the inner member of the flexible elongate member. In some other examples, establishing electrical communication may include contacting each end of the plurality of ultrasound transducer elements to a respective one of a plurality of outer bond pads disposed on an outer diameter of the integrated circuit controllers.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
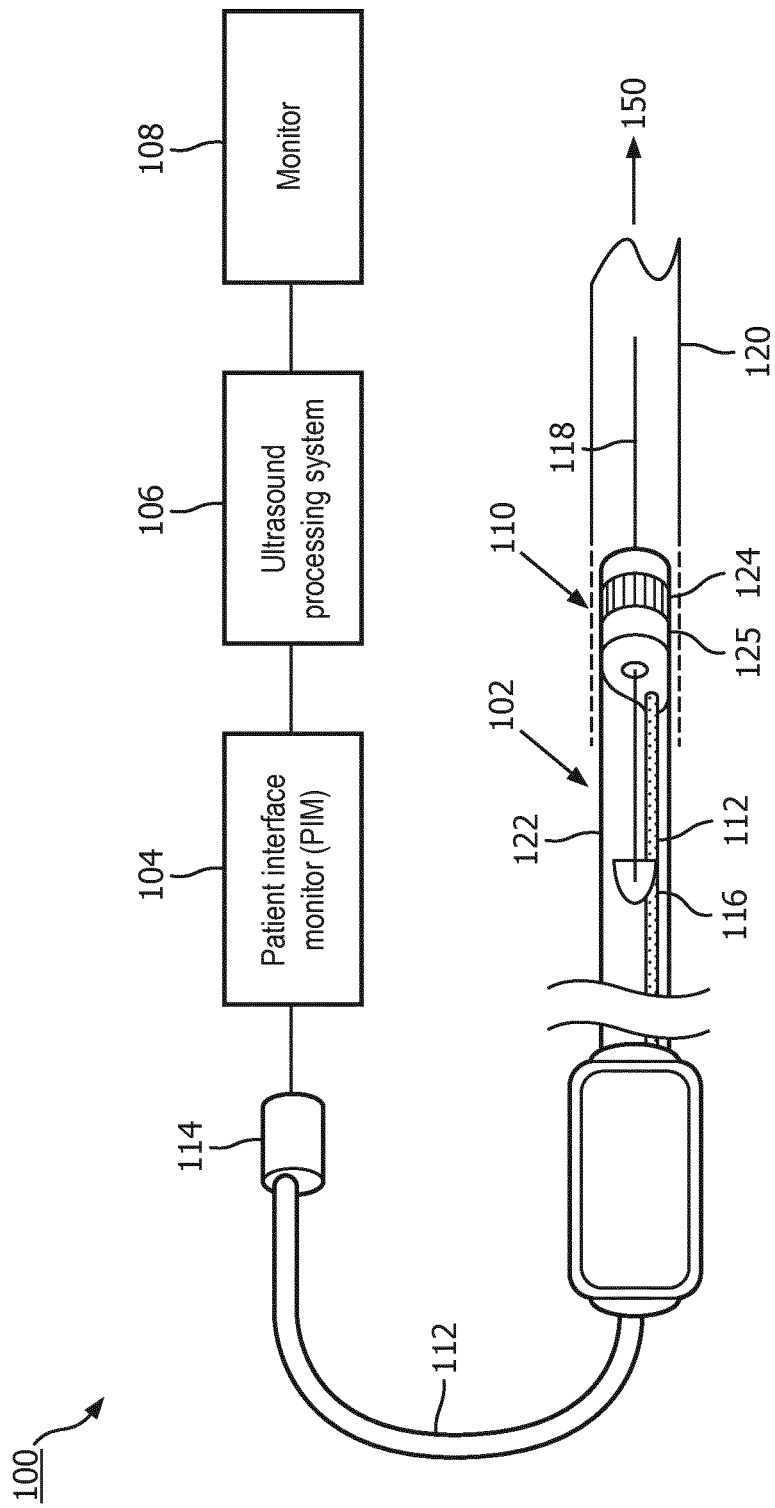
FIG. 1 is a diagrammatic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the imaging system is described in terms of cardiovascular imaging, it is understood that it is not intended to be limited to this application. The system is equally well suited to any application requiring imaging within a confined cavity including a lumen within a body. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

According to aspects of the present disclosure, annularly-shaped integrated circuit controllers are implemented in an ultrasound imaging assembly of an intraluminal imaging device. The annularly-shaped controllers reduce the stiff length compared to imaging assemblies with rectangular-shaped controllers. According to the present disclosure, a catheter based imaging device is small enough and manoeuvrable enough to be able to reach target sites within the body that may be accessed via small diameter, tortuous channels, such as blood vessels. The size of a catheter based imaging device, which may limit accessing of the target sites, is often a function of the size of the control circuitry to operate the imaging sensor on the device. In the instance of solid state IVUS for example, multiple integrated circuit controllers (ASICs) may operate as multiplexers that are necessarily very proximate to the ultrasound transducer elements. Annularly-shaped ASICs advantageously improve the flexibility and manoeuvrability of the imaging device.

FIG. 1 is a diagrammatic schematic view of an intraluminal imaging system 100, according to aspects of the present disclosure. The intraluminal imaging system 100 may include a solid-state or phased array intraluminal ultrasound imaging device 102 in the form of a catheter or guide catheter, a patient interface module (PIM) 104, an ultrasound computing device 106, and a display 108.

The intraluminal imaging device 102 includes a flexible elongate member 122 that is configured to be inserted into a lumen, e.g., a vessel 120, within a body of a patient. The flexible elongate member 122 can include one or more elongate members that are formed of a flexible material, such as a plastic or a polymer. The flexible elongate member 122 can have generally tubular shape with a circular cross-sectional profile. In some embodiments, an inner tubular member can be concentrically positioned within an outer tubular member. The flexible elongate member 122 may include a proximal portion, a central portion, a distal portion, and a longitudinal axis 150. The central portion extends between the proximal portion and the distal portion. The longitudinal axis 150 can be a central longitudinal axis in some embodiments. A connector 114 can be disposed at the proximal portion of the flexible elongate member. A imaging device or imaging assembly 110 can be disposed at the distal portion of the flexible elongate member 122. The imaging assembly 110 includes an ultrasound transducer array 124 in communication with one or more controllers 125. The array 124 is positioned around the central longitudinal axis 150. As described herein, the one or more controllers 125 are annularly or ring shaped. The central longitudinal axis 150 can extend through an opening defined by the one or more controllers 125.

At a high level, the ultrasound imaging assembly 110 emits ultrasonic energy from the transducer array 124 included in imaging assembly 110 and mounted near a distal end of the intraluminal device 102. The ultrasonic energy is reflected by tissue structures in the medium, such as a vessel 120, surrounding the imaging assembly 110, and the ultrasound echo signals are received by the transducer array 124. The PIM 104 transfers the received echo signals to the ultrasound computing device 106 where the ultrasound image is reconstructed and displayed on the display or monitor 108. The ultrasound computing/processing device 106 or computer can include one or more processors and any suitable memory. The ultrasound computing device 106 can be operable to facilitate the features of the intraluminal imaging system 100 described herein. For example, a processor of the computing device 106 can execute computer readable instructions stored on the non-transitory tangible computer readable medium of the computing device 106.

The PIM 104 facilitates communication of signals between the ultrasound processing system 106 and the imaging assembly 110 included in the imaging device 102. In some embodiments, the PIM 104 performs preliminary processing of the echo data prior to relaying the data to the ultrasound computing device 106. In examples of such embodiments, the PIM 104 performs amplification, filtering, and/or aggregating of the data. In some embodiments, the PIM 104 also supplies high- and low-voltage DC power to support operation of the intraluminal imaging device 102 including circuitry within the imaging assembly 110.

The ultrasound computing device or console 106 receives the echo data from the imaging assembly 110 of the intraluminal imaging device 102 by way of the PIM 104 and processes the data to reconstruct an image of the tissue structures in the medium surrounding the imaging assembly 110. The ultrasound computing device 106 outputs image data such that an image of the vessel 120, such as a cross-sectional image of the vessel 120, is displayed on the display 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or any suitable lumen inside the body. The intraluminal imaging device 102 is an intravascular imaging device or IVUS imaging device in some embodiments. The intraluminal imaging device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the heart, chambers or other parts of the heart, and/or other systems of the body. The intraluminal imaging device 102 may be used to examine any lumen in the above anatomical locations. In addition to natural structures, the intraluminal imaging device 102 may be used to examine man-made structures such as, but without limitation, heart valves, stents, shunts, filters and other devices.

In some embodiments, the intraluminal imaging device 102 includes some features similar to traditional solid-state intravascular imaging catheters, such as the EagleEye® catheter available from Volcano Corporation and those disclosed in U.S. Pat. No. 7,846,101 hereby incorporated by reference in its entirety. For example, the intraluminal imaging device 102 includes the imaging assembly 110 near a distal end of the imaging device 102 and a transmission line cable 112 extending along the longitudinal body of the imaging device 102. The transmission line bundle or cable 112 can include a plurality of conductors, including one, two, three, four, five, six, seven, or more conductors. The cable 112 facilitates communication of electrical signals between the imaging assembly 110 and the ultrasound computing device 106.

The transmission line cable 112 terminates in a PIM connector 114 at a proximal end of the imaging device 102. The PIM connector 114 electrically couples the transmission line cable 112 to the PIM 104 and physically couples the intraluminal imaging device 102 to the PIM 104. In some embodiments, the intraluminal imaging device 102 further includes a guide wire exit port 116. Accordingly, in some instances the intraluminal imaging device is a rapid-exchange catheter. The guide wire exit port 116 allows a guide wire 118 to be inserted towards the distal end in order to direct the imaging device 102 through the vessel 120.

The system 100, the intraluminal device 102, the imaging assembly 110, and/or other components of the system 100 can include features similar to those described in U.S. application Ser. No. 14/137,269, filed Dec. 20, 2013, the entirety of which is hereby incorporated by reference.

Figure 2:
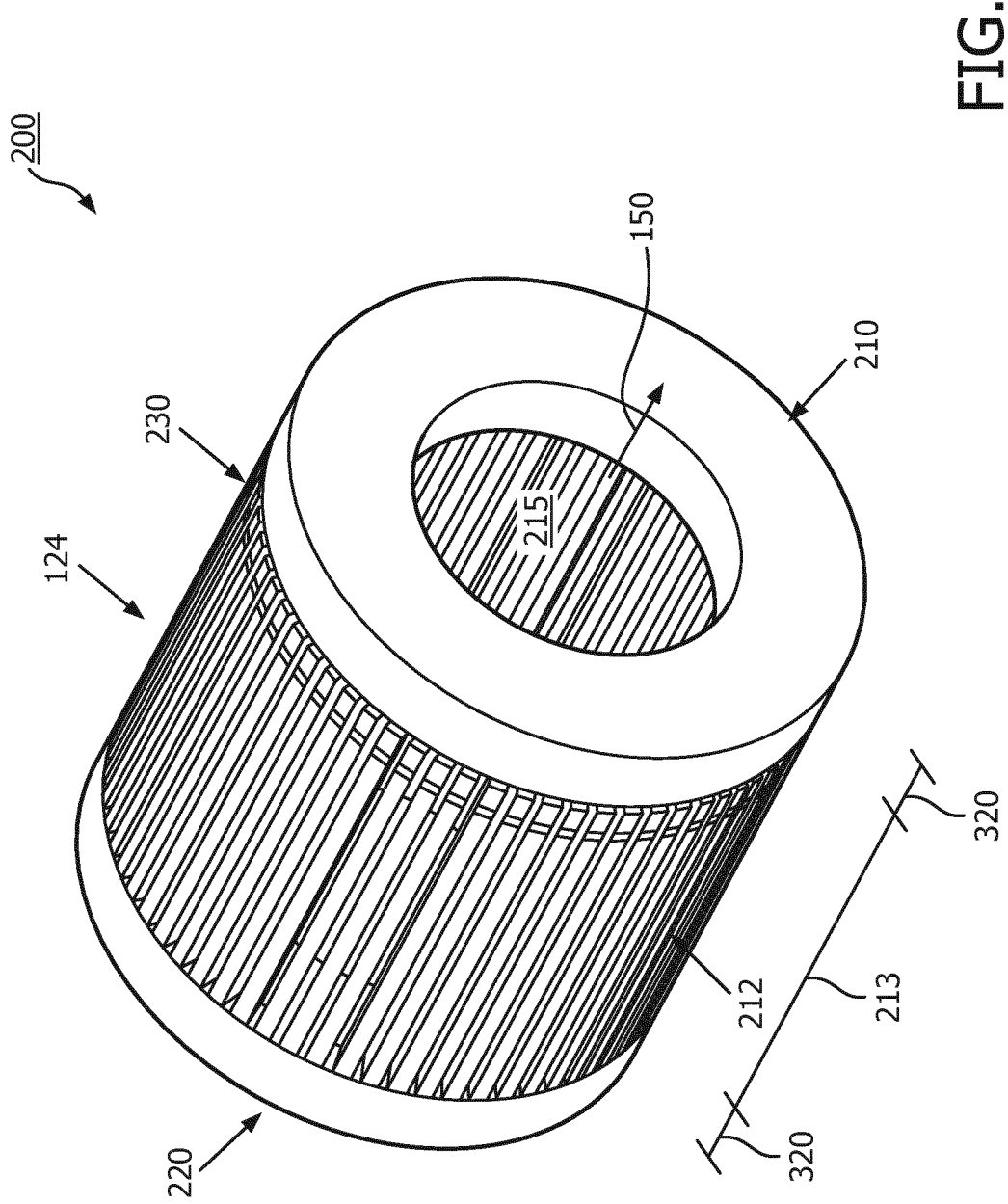
FIG. 2 is a diagrammatic isometric view of an imaging assembly in a rolled configuration, according to aspects of the present disclosure.

FIG. 2 is a diagrammatic isometric view of an imaging assembly 200 in a rolled configuration, according to aspects of the present disclosure. The imaging assembly 200 can include features similar to those described with respect to the imaging assembly 110 of FIG. 1. The imaging assembly 200 includes the transducer array 124 and integrated circuit controllers 210, 220. The transducer array 124 includes a plurality of imaging elements, e.g., ultrasound transducer elements 212. Generally, the array 124 can include any suitable number of transducers, including between approximately 30 transducer and approximately 150 transducers, including values such as 32 transducers, 64 transducer, 128 transducers, etc. The integrated circuit controllers 210, 220 can be electrically and mechanically coupled to the transducer elements 212 of the transducer array 124.

The integrated circuit controllers 210, 220 can be application specific integrated circuits (ASICs) in some embodiments. The controllers 210, 220 facilitate operation of the ultrasound transducer elements 212 and include any suitable circuitry, such as multiplexing circuitry. One or both of the integrated circuit controllers 210, 220 can receive configuration data and transmit triggers received via the cable 112, drive the elements 212 in transmit mode to emit ultrasonic energy, control the elements 212 in receive mode to receive reflected ultrasound echoes, and/or transmit echo data on the cable 112 to the computing device 106. While two controllers 210, 220 are illustrated in FIG. 2, it is understood that the imaging assembly 200 can include one, two, three, four or more controllers. In that regard, more controllers provide more surface area for circuitry used to control operation of array 124, such as multiplexing circuitry. In some embodiments, one of the controllers is a master controller that communicates directly to the cable 112 and communicates indirectly with the transducer elements 212 via one or more slave controllers. One or more of the controllers can be slave controllers that communicate directly with the transducer elements 212 and communicate indirectly to the cable 112 via the master controller. In some embodiments, both of the controllers 210, 220 communicate directly with the ultrasound elements 212 and the cable 112. In some embodiments, both controllers 210, 220 control all of the transducer elements 212 together. In other embodiments, each controller 210, 220 controls a subset of the transducer elements 212.

One or more controllers can be positioned proximally and/or distally of the transducer array 124. In the illustrated embodiment of FIG. 2, the controller 210 is positioned proximally of the transducer array 124, and the controller 220 is positioned distally of the transducer array 124. The transducer elements 212 extend longitudinally between the controllers 210, 220.

The controllers 210, 220 are annularly-shaped or ring-shaped. For example, the outer surface of the controllers 210, 220 can be a cylindrically shaped. A cylindrical opening 215 extends longitudinally through the controllers 210, 220 to create the annulus or ring shape. The opening 215 can be aligned with the longitudinal axis 150. In such embodiments, such the opening 215 is in the center of the controllers 210, 220 and the longitudinal axis 150 extends through the center of the controllers 210, 220 and the opening 215. The cross-section of the controllers 210, 220 may be formed of concentric circles.

The controllers 210, 220 have a dimension 320 in the longitudinal direction, along the length of the intraluminal device 102. The dimension 320 can be between approximately 120 µm and approximately 150 µm in some embodiments. The transducer elements have a dimension 213 in the longitudinal direction, along the length of the intraluminal device 102. The dimension 213 can be between approximately 1 mm in some embodiments. The total length of the imaging assembly 200, including the controllers 210, 220 and the transducer elements 212, can be approximately 1.5 mm or less in some embodiments.

In some embodiments, the integrated circuit controllers 210 and 220 are made of silicon and/or other suitable materials. For example, the controllers 210, 220 can be silicon based dies. Existing rectangular controller are shaped using silicon dicing techniques. Obtaining circular shapes with dicing is not possible. Because the dimension 320 of the of the controllers 210, 220 is between approximately 120 µm and approximately 150 µm, the controllers 210, 220 can be shaped using a silicon etching processes.

As shown in FIG. 2, the controllers 210, 220 extend primarily in a plane perpendicular or orthogonal to the longitudinal axis 150. In contrast, existing devices include controllers that primarily extend longitudinally such that existing imaging assembly have a length of approximately 10 mm. The arrangement of the controllers 210, 220 advantageously reduces the stiff length of the imaging assembly. In some embodiments, the stiff length of the imaging assembly may be less than 1.5 mm and may make it easier to pass the imaging device through body lumens include changes of direction.

The transducer elements 212 can be lead zirconate titanate (PZT) elements in some embodiments. The integrated circuit controllers 210 and 220 may apply an excitation voltage to the ultrasound transducer elements 212. For example, the integrated circuit controllers 220 may apply a voltage to an electrode of each ultrasound transducer elements 212 closer to the longitudinal axis 150, and the integrated circuit controllers 210 may apply a voltage to an electrode of each ultrasound transducer elements 212 further from the longitudinal axis 150. As shown, each ultrasound transducer element 212 includes a proximal isolation cut 230 such that the proximal integrated circuit controllers 210 may only be in electric contact with the electrode of the ultrasound transducer elements 212 closer to the longitudinal axis 150. A similar distal isolation cut 230 may exist on the electrode of the ultrasound transducer elements 212 closer to the longitudinal axis 150 such that the distal integrated circuit controllers 220 may only be in electric contact with the face of the ultrasound transducer elements 212 farther from the longitudinal axis 150.

Figure 3:
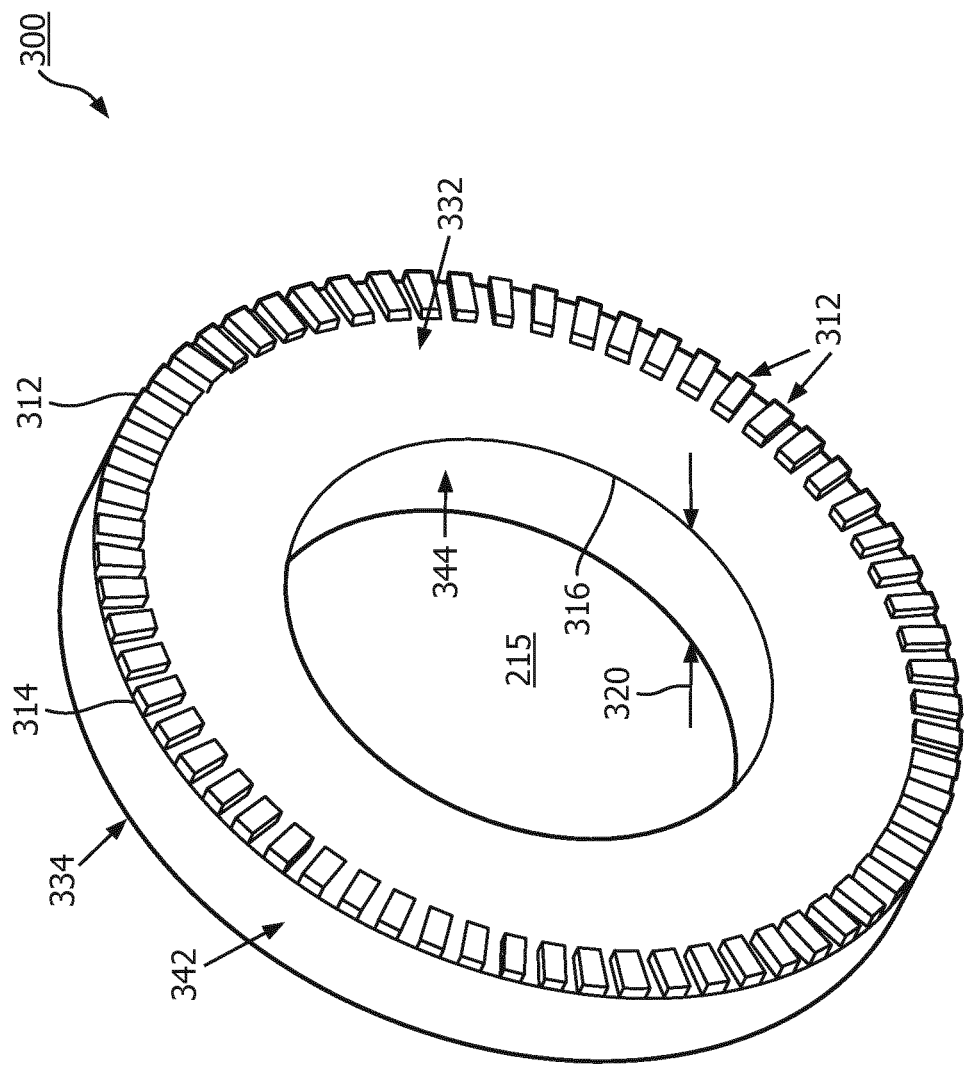
FIG. 3 is a diagrammatic isometric view of an annular integrated circuit controller of an imaging assembly, according to aspects of the present disclosure.

FIG. 3 is a diagrammatic isometric view of an annular integrated circuit controller 300, according to aspects of the present disclosure. The controller 300 can be similar to the controllers 210, 220 described with respect to FIG. 2. The controller 300 includes an outer diameter 314 and an inner diameter 316. In some embodiments, the outer diameter 314 is between approximately 0.032" and 0.131", for example. In some embodiments, the inner diameter 316 can is between approximately 0.01" and 0.065", for example. The dimensions of the controller 300 can be selected such that the intravascular device 102 has a diameter between approximately 2 Fr and approximately 10 Fr. The controller 300 also includes an outer surface 342 and an inner surface 344 that extend longitudinally along length of the device 102. As described herein, a flexible substrate can be positioned on the outer surface 342. The inner surface 344 can include or more bond ponds in contact with conductive traces of an inner flexible elongate member. The inner diameter 316 and the inner surface 344 define the opening 215.

The integrated circuit controller 220 includes outer bond pads 312 distributed along the outer diameter 314. The bond pads 312 are formed of an electrically conductive material such as a metal, including gold, silver, or copper, or a metal alloy, and/or any other suitable material. The bond pads 312 can be positioned around the outer diameter 314 using, e.g., a pick and place process, or by a bumping process associated with silicon based surface mount technology. The quantity of bond pads 312 can equal a quantity of transducer element 212. For example, the controller 300 can include sixty-four bond pads when the array 124 includes sixty-four bond pads. The bond pads 312 are rotationally aligned with the transducers 212. Each bond pad 312 can be electrically coupled to an individual transducer element 212. In some embodiments, each bond pad 312 is directly or indirectly in contact with a respective transducer element 212. A surface 214 (FIG. 5B) of the transducer elements 212 can contact the bond pad 312. For example, a gold bond pad 312 can be in contact with a gold electrode of the transducer element 212, which provides good electrical conductivity between the components. In such embodiments, the bond pads 312 can be cold welded to the transducer elements 212. In other embodiments, an electrically conductive adhesive, such as silver epoxy, can be used to mechanically and/or electrically couple the bond pad 312 and the transducer element 212. Bond pads 312 placed toward the outer perimeter of the integrated circuit controllers may provide a way in which the individual ultrasound transducer elements 212 can make electrical contact to the die without the need for a flex circuit, in some embodiments.

As shown in FIG. 3, the controller 300 includes faces 332, 334. In some embodiments, such as when the controller 300 is a distal controller (e.g., distal controller 220 of FIG. 2), the face 332 is a proximal face and the face 334 is a distal face. The bond pads 312 can be positioned on the proximal face 332 (FIG. 3) of the distal controller 220 (FIG. 2). The bond pads 312 can be positioned on the distal face 334 (FIG. 3) of the proximal controller (FIG. 2). In this manner, the bond pads 312 can be disposed adjacent to and/or in contact with the transducer elements 212 positioned between the proximal and distal controllers.

Figure 4:
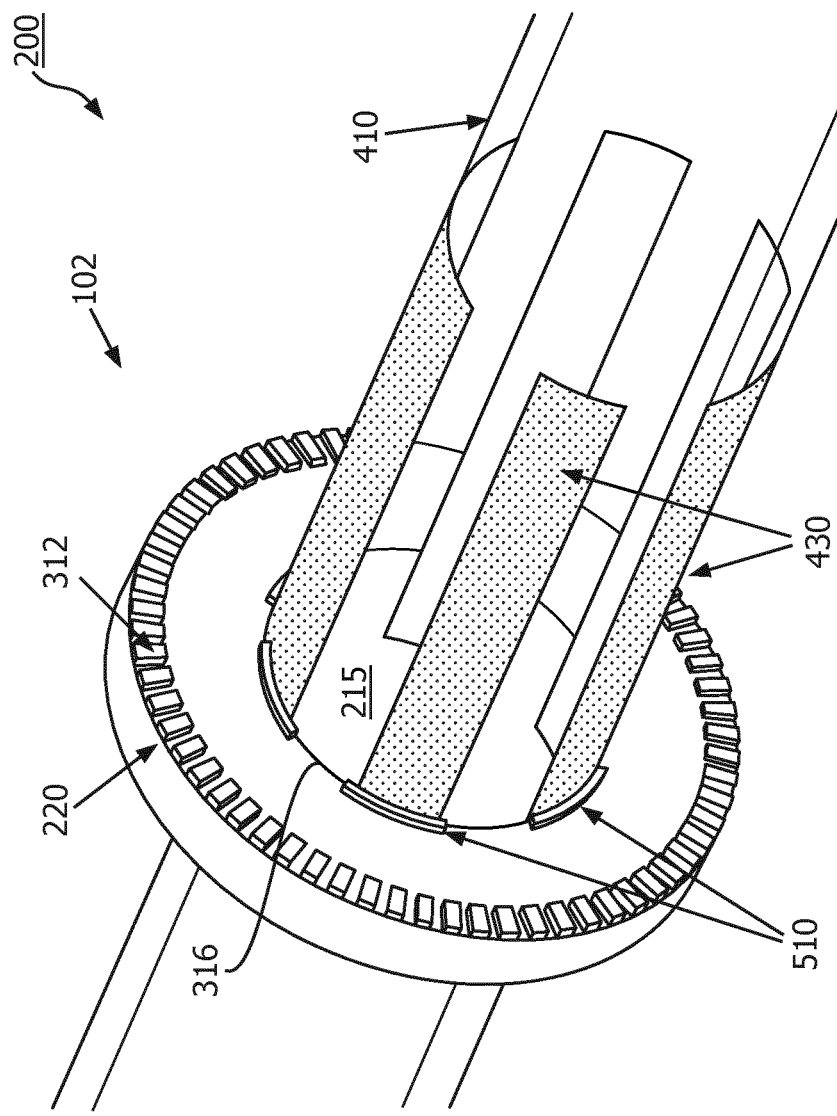
FIG. 4 is a diagrammatic isometric view of a distal portion of an intraluminal imaging device including an integrated circuit controller and an inner flexible elongate member with a conductive trace, according to aspects of the present disclosure.

FIG. 4 is a diagrammatic isometric view of a distal portion of an intraluminal imaging device 102 including the imaging assembly 200 during a step of manufacturing, according to aspects of the present disclosure. An inner flexible elongate member 410 extends through the opening 215 of the controller 220. As result, the inner member 410 can be mechanically and/or electrically coupled to the controller 220. In some examples, the inner member 410 may create an inner lumen 415 around the longitudinal axis 150. The guide wire 118 (FIG. 1) can extend through the lumen 415 parallel to or coaxial with the longitudinal axis 150. The inner member 410 may be an elongate tubular component formed of a flexible plastic or polymer material.

Electrically conductive traces 430 are provided on an outer surface of the inner member 410. The inner diameter 316 of the controller 220 includes one or more bond pads 510. Any suitable number of conductive traces 430 and bond pads 510 is contemplated. In the illustrated embodiment, six bond pads 510 and six conductive traces 430 are provided. In some examples, the inner pond pads 510 and the conductive traces 430 can be made of any electrically conductive material, such as a metal including gold, silver, or copper, or a metal alloy, and/or any other suitable material. The bond pads 510 can be distributed around the inner diameter 316. In some embodiments, the bond pads 510 extend along the inner surface 344 of the controller 220. Additional pads 510 placed at the inner perimeter of the integrated circuit controller may provide a location for additional connections between the integrated circuit controllers that are not associated with the connection to the ultrasound transducer elements.

When the inner member 410 extends through the opening 215 of the controller 220, the bond pads 510 contact the conductive traces 430. The inner bond pads 510 electrically connect to the conductive traces 430 and transmit signals through the conductive traces 430. In some examples, both the proximal and distal controllers 210 and 220 include inner bond pads 510 that are in contact with the conductive traces 430. In that regard, the controllers 210, 220 are in electrical communication via the conductive traces 430. The controllers 210, 220 may communicate via electrical signals through their respective inner bond pads and the conductive traces 430. In some other examples, electrical power may be transmitted through the inner bond pads and the conductive traces 430 between the proximal and distal integrated circuit controllers 210, 220. In some other examples, a connection to electrical ground is provided through the inner bond pads and 510 the conductive traces 430 between the proximal and distal integrated circuit controllers 210, 220. In some embodiments, in lieu of or in addition to the conductive traces 430, one or more of the transducer elements 212 can be used for electrical communication between the controllers 210, 220.

Figure 5A:
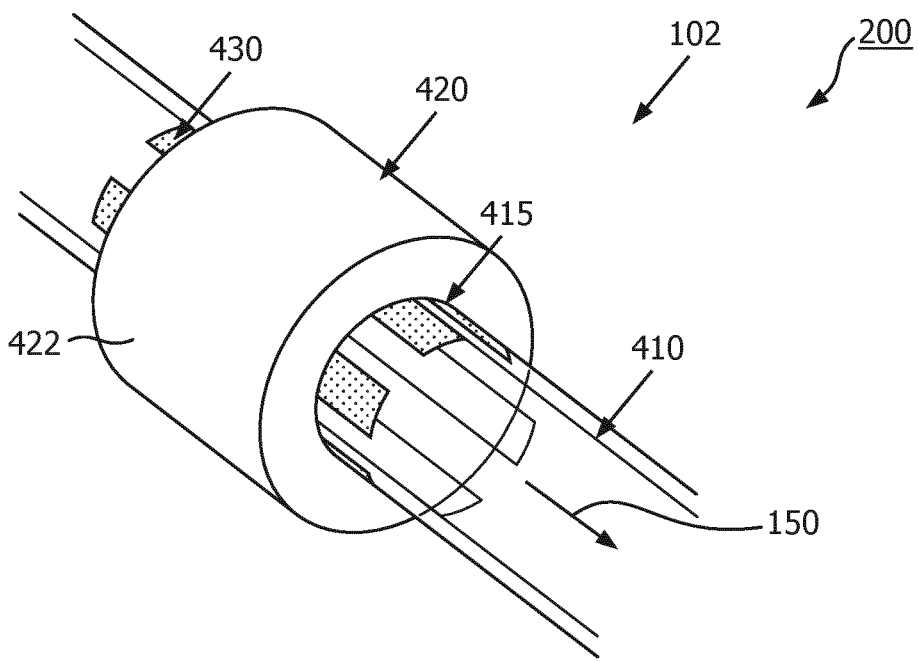
FIG. 5A is a diagrammatic isometric view of a distal portion of an intraluminal imaging device including an acoustic backing material and an inner flexible elongate member, according to aspects of the present disclosure.

FIG. 5A is a diagrammatic isometric view of a distal portion of the intraluminal imaging device 102 including the imaging assembly 200 during a step of manufacturing, according to aspects of the present disclosure. Acoustic backing material 420 and the inner member 410 are illustrated. The acoustic backing material 420 may be disposed around the longitudinal axis 150 and may take an annular form. For example, the inner member 410 can extend longitudinally through the lumen 415 of the acoustic backing material 420. In that regard, the acoustic backing material 420 may be a pre-formed solid or semi-solid. For example, the acoustic backing material 420 can be molded into the annular shape illustrated in FIG. 5A. A pre-formed acoustic backing material may advantageously allow for a more efficient manufacturing process because the solid or semi-solid mass that maintains its shape can be positioned around the inner member 410. The pre-formed/molded backing material 420 can include a cured epoxy or adhesive material that is loaded with both scattering particles (such as hollow microspheres and particles that have high density such as to raise the overall acoustic impedance of the backing material to facilitate good acoustic coupling between the PZT and the backing material, and/or any other suitable material, for example, tungsten carbide to form a de-matching layer or silver filled epoxy to provide a common ground. In other embodiments, a liquid acoustic backing material that is later cured into a solid is used. The acoustic backing material 420 is material that attenuates the acoustic energy emitted by the array 124 and prevents acoustic propagation in undesirable directions, such as towards the longitudinal axis 150.

Figure 5B:
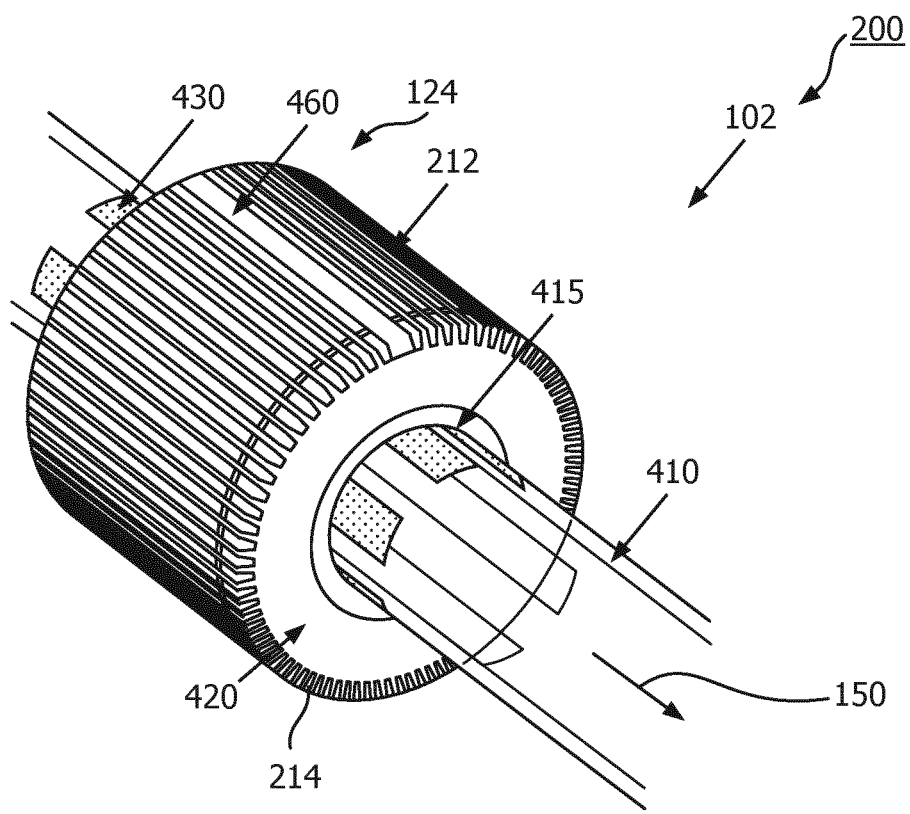
FIG. 5B is a diagrammatic isometric view of a portion of an intraluminal imaging device including an ultrasound transducer array, an acoustic backing material, and an inner flexible elongate member, according to aspects of the present disclosure.

FIG. 5B is a diagrammatic isometric view of a distal portion of an intraluminal imaging device 102 including the imaging assembly 200 during a step of manufacturing, according to aspects of the present disclosure. FIG. 5B illustrates the acoustic backing material 420, the inner member 410 of FIG. 5A. Diagram 450 additionally includes the transducer array 124 disposed around the backing material 420. As described, the transducer array 124 may include the plurality of ultrasound transducer elements 212. The transducer elements 212 can be positioned on a surface 422 (FIG. 5A) of the backing material 420. In some examples, a flexible substrate (FIG. 8A), including the ultrasound transducer elements 212 formed on the flexible substrate and/or otherwise attached to the substrate, is rolled around the backing material 420 and the longitudinal axis 150. In other embodiments, the imaging assembly 110 omits the flexible substrate and the transducer elements 212 are directly positioned around the backing material 420 and the longitudinal axis 150 using, e.g., a pick and place process. An adhesive may be disposed between the transducer elements 212 and the pre-formed backing material 420 to create a mechanical bond between the components. In some examples, a transducer element (e.g., PZT element) or some other electrically conductive material 460 may provide an alternative line of electrical communication that provides communication of power, signals, and/or any suitable type of data between the proximal and distal ASICs 210 and 220. In some embodiments, the conductive/transducer element 460 can be implemented in the imaging assembly to provide electrical communication between the controllers 210, 220 in lieu of or in addition to the conductive traces 430.

Figure 6:
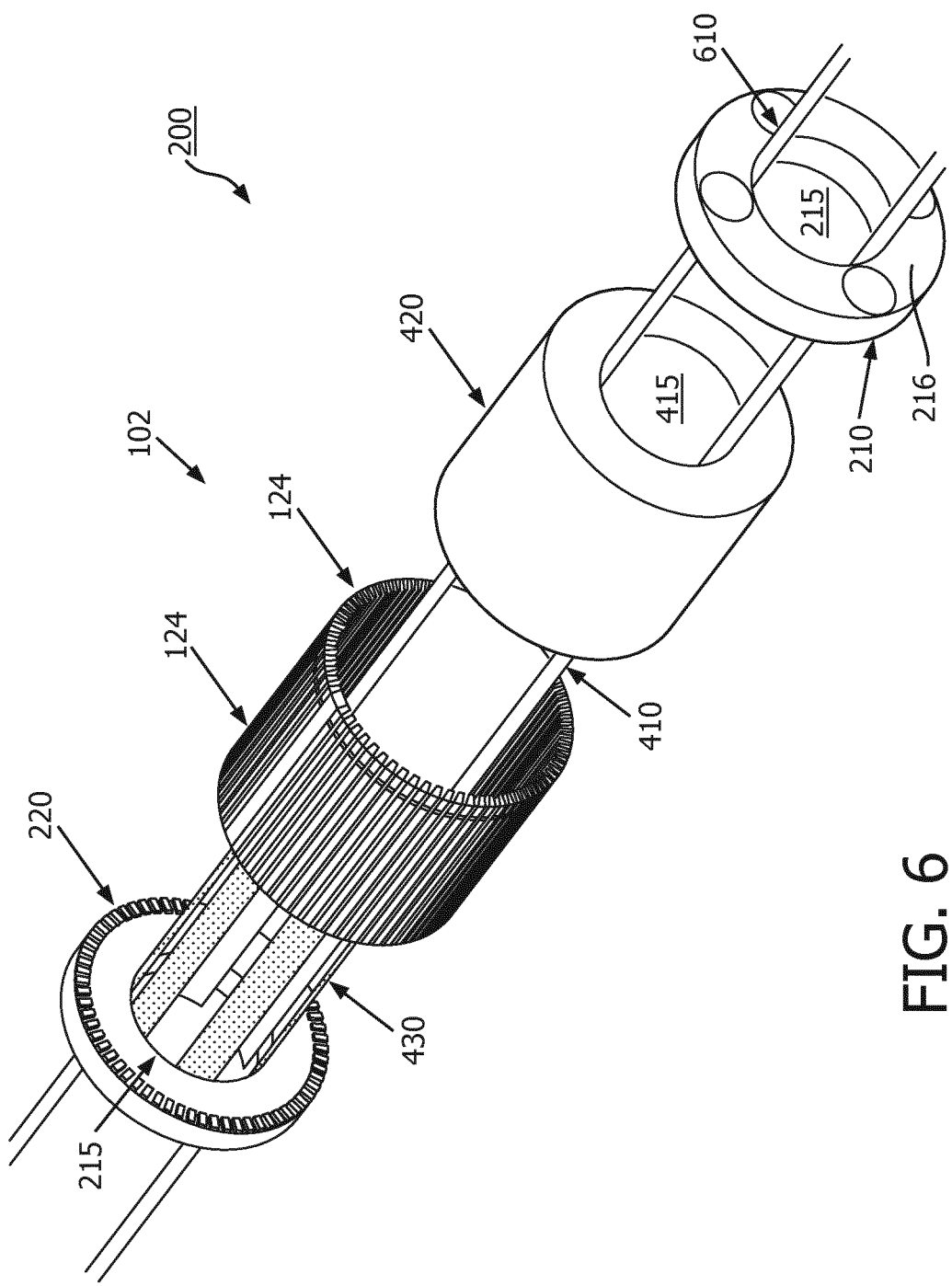
FIG. 6 is a diagrammatic isometric view of components of an imaging assembly illustrated in an exploded format along an inner flexible elongate member, according to aspects of the present disclosure.

FIG. 6 is a diagrammatic isometric view of a distal portion of intraluminal imaging device 102, including components of the imaging assembly 200 illustrated in an exploded format along an inner flexible elongate member 410, according to aspects of the present disclosure. The imaging assembly 200 includes the transducer array 124, the proximal and distal integrated circuit controllers 210 and 220. As described with respect to FIG. 5B, the transducer array 124 is positioned around the acoustic backing material 420. The inner member 410 extends through lumen 215 of the controllers 210, 220, and the lumen 415 of the acoustic backing material 420. The conductive traces facilitate electrical communication between the controllers 210, 220.

Figure 7:
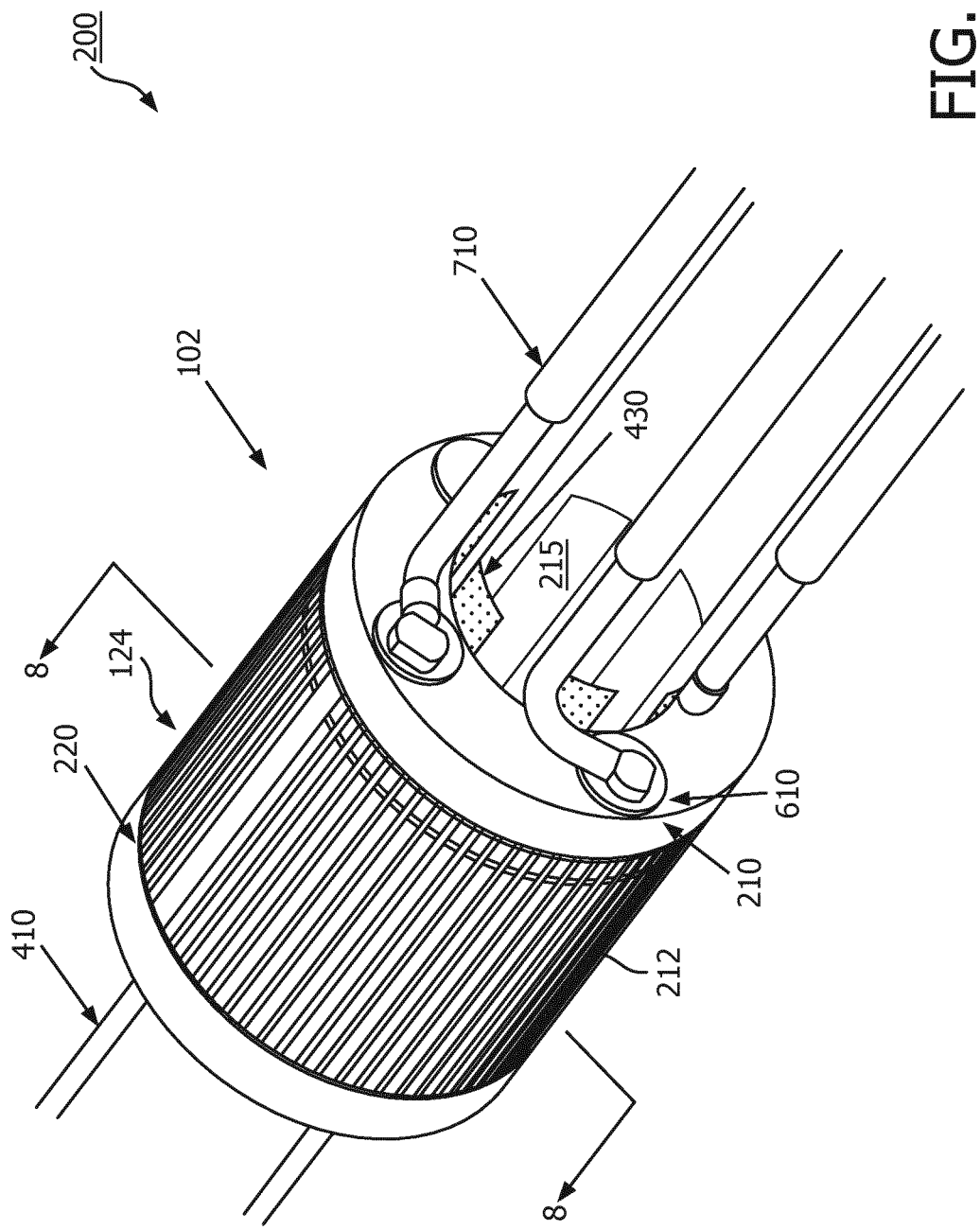
FIG. 7 is a diagrammatic isometric view of a distal portion of an intraluminal imaging device including conductors coupled to an integrated circuit controller of an imaging assembly, according to aspects of the present disclosure.

FIG. 7 is a diagrammatic isometric view of a distal portion of an intraluminal imaging device 102 including the imaging assembly 200 during a step of manufacturing. FIG. 7 illustrates ultrasound imaging array 124 positioned between the controllers 210, 220. The inner member 410 extends through the lumens 215 of the controllers 210, 220. In some embodiments, the array 124 and the controller 210, 220 may be manufactured with a compression fit for mechanical attachment and/or electrical communication. For example, the controllers 210, 220 can be pressed against the transducer elements. Adhesive between the controllers 210, 220 and the inner member 410 can fix the longitudinal positions of the controllers 210, 220 along the inner member 410. Acoustic backing material can be disposed in the space defined by the inner member, the controllers 210, 220, and the array 124. In embodiments in which a liquid backing material is used, the liquid backing material can be delivered into the space such that it contacts surfaces of the inner member, the controllers 210, 220, and the array 124. When the liquid backing material cures and harden, the components of the imaging assembly 200 and the inner member 410 are bonded together. In other embodiments, adhesive can be used to bond the pre-formed acoustic backing material, the inner member, the controllers 210, 220, and the array 124 together.

FIGS. 6 and 7 also illustrate bond pads 610 provided on a proximal surface 216 of the proximal controller 210. The bond pads 610 can be distributed around the circumference of the controller 210. The bond pads 610 are formed of an electrically conductive material such as a metal, including gold, silver, or copper, or a metal alloy, and/or any other suitable material. The bond pads 610 can be positioned around the circumference of the controller 210 using, e.g., a pick and place process. In some embodiments, the back substrate bond pads 610 provide electrical connections to the controller 210 through vias at the back surface of a substrate. The bond pads 610 are electrically and mechanically coupled to conductors 710 of the cable 112 (FIG. 1). Any suitable number of conductors can be provided including one, two, three, four, five, six, seven, or more conductors. The conductors 710 can be control and signal lines that facilitate communication of power, signals, and/or any suitable type of data between the imaging assembly 200 and the computing device 106. For example, control and signal lines 710 facilitate communication of electrical signals between the imaging assembly 110 and the ultrasound computing device 106. In some examples, the control and signal lines 710 may provide electrical power to one or both of the integrated circuit controllers 210 and 220. The electrical connections of the signal lines 710 to the back substrate bond pads 610 may be made by means of heat or thermosonic welds, for example. The conductors 710 extend along the length of the flexible elongate member 122 between the imaging assembly and the connector 114 (FIG. 1). Back substrate bond pads 610 on the proximal side of the integrated circuit controllers provide the connection for control and signal lines and also ground and power connections to the integrated circuit controllers, in some embodiments.

In some embodiments, the bond pads 610 are omitted, and the conductors 710 are electrically and/or mechanically coupled to the conductive traces 430 of the inner member 410. As described herein, the controllers 210, 220 are in communication with the conductive traces 430. The computing device 106 can also be in communication with the imaging assembly 200 via the conductive traces 430.

Figure 8A:
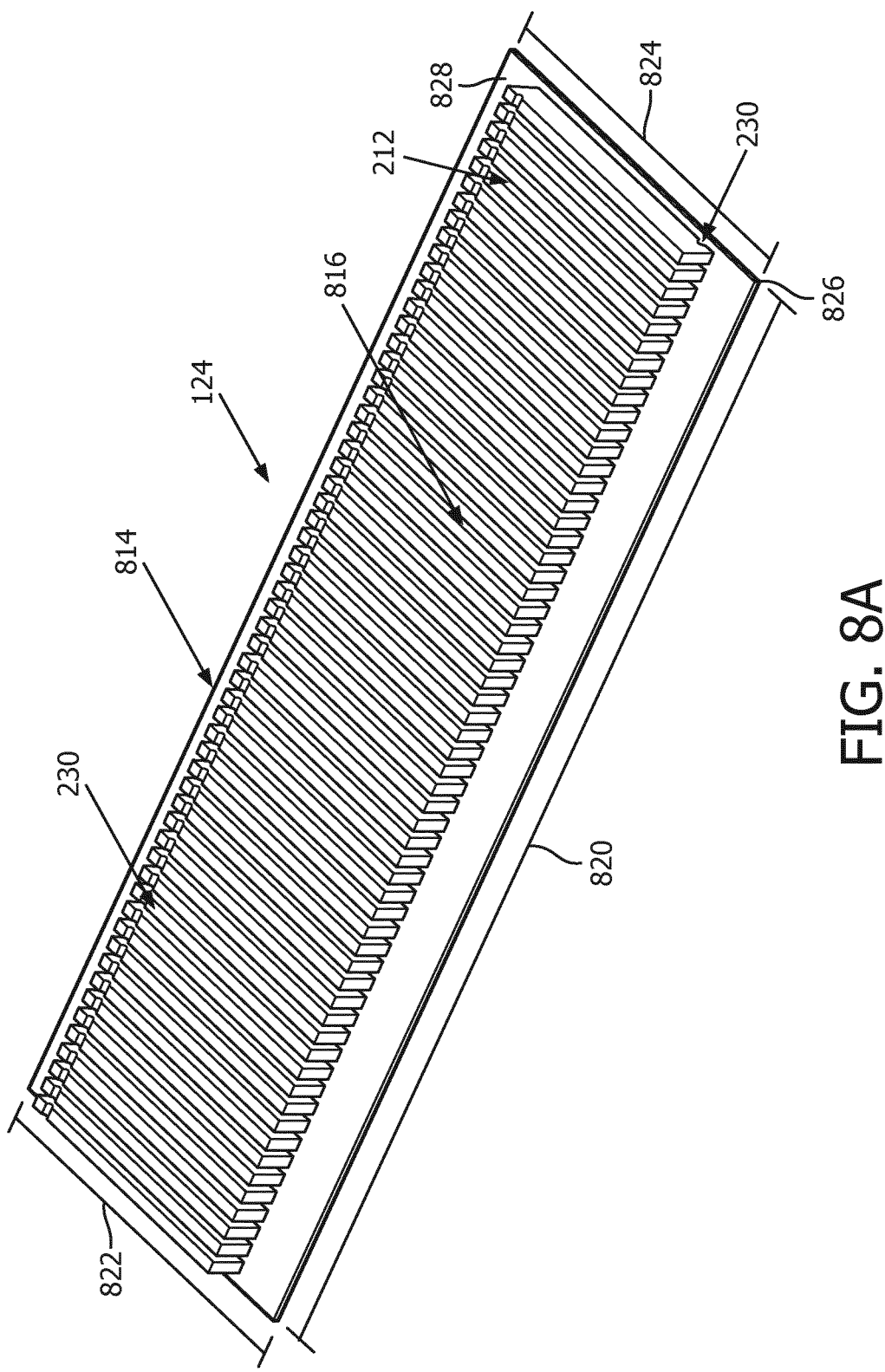
FIG. 8A is a diagrammatic isometric view of an ultrasound transducer array and flexible substrate in a flat configuration, according to aspects of the present disclosure.

FIG. 8A is a diagrammatic isometric view of the ultrasound transducer array 124 and a flexible substrate 814 in a flat configuration, according to aspects of the present disclosure. The flexible substrate 814 can be a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont).

In the flat configuration illustrated in FIG. 8A, the flex substrate 814 has a generally rectangular shape. As shown and described herein, the flexible substrate 814 is configured to be wrapped to form a cylindrical toroid in some instances. Therefore, the thickness of the film layer of the flexible substrate 814 can be related to the degree of curvature in the final assembled scanner assembly 200. In some examples, the flexible substrate thickness may provide good acoustic matching between the PZT and the material on the exterior of the flexible substrate, usually blood or a liquid and the thickness may depend upon the frequency of operation of the transducer array. The flexible substrate thickness can be selected to provide good acoustic matching between the PZT and the material on the exterior of the flex, such as blood or liquid. It is generally accepted that a matching layer thickness corresponds to the length of one quarter wavelength in the matching material. As such, the thickness of choice can depend upon the frequency of operation of the transducer array. In some embodiments, the film layer 814 is between 5 µm and 100 µm, with some particular embodiments being between 12.7 µm and 25.1 µm. In some embodiments, the flexible substrate 814 can omit conductive traces such that the flexible substrate 814 may provide only support for the elements 212 of the array 124. This allows for imaging assembly 200 to be manufactured in a more cost efficient manner. In other embodiments, the flexible substrate 814 can include conductive traces to facilitate communication between one or more the elements 212, and the controllers 210, 220.

According to an exemplary embodiment, during manufacturing of the imaging assembly 200, an undiced block of PZT is formed on and/or otherwise mechanically coupled to the substrate 814, such as using an adhesive. The PZT can have a width 820 of approximately 3 mm, a length 824 of approximately 1 mm, and a depth of approximately 70 μm, for example. The length 822 of the flexible substrate 814 can be greater than the length 824 of the PZT block by approximately 250 μm such that the length 822 of the substrate 814 is approximately 1.25 mm in some examples. The lengths 822 and 824 can be representative of a longitudinal direction, along the length of the device 102 in some instances. The PZT block can be positioned on the substrate 814 such that an equal length (e.g., 125 μm) of substrate is disposed on the proximal side 826 and the distal side 828 of the PZT block. When the flexible substrate 814 and array 124 are rolled into a cylindrical configuration, as shown in the cross-sectional view of FIG. 10, the proximal and distal portions 826, 828 of the substrate 814 can be used to form a lap joint with the controllers 210, 220 in some embodiments. For example, adhesive can be positioned between the proximal and distal portions 826, 828 of the substrate 814 and the outer surfaces 342 of the controllers 210, 220 to advantageously provide strong mechanical coupling between the substrate 814 and the controllers 210, 220.

Referring again to FIG. 8A, the width of the flexible substrate 814 can be substantially similar to the width 820 of the PZT block such that none or only a small portion of flexible substrate extends beyond the PZT block. When the flexible substrate 814 and array 124 are rolled into a cylindrical configuration, as shown in the cross-sectional view of FIG. 8B, the edges of the substrate 814 can form a butt joint 455, in some embodiments. Utilizing the butt joint 455 between the edges of the substrate 814 avoid the increased thickness associated with a lap joint. A lap joint would also result in a double acoustic matching layer, which may not provide the desired transmission properties for ultrasonic energy.

After being attached to the flexible substrate 814, the PZT block is then diced along the cuts 816 into individual ultrasound transducer elements 212 that form the array 124. The transducer array 800 may also include the isolation cuts 230 through the upper and lower electrodes of each ultrasound transducer element 212, in some embodiments. The isolation cuts 230 advantageously prevent an electrical short circuit when the transducer elements 212 are electrically coupled to the controllers 210, 220. In some embodiments, the ultrasound transducers, e.g., PZT elements may have 'wrap around' electrodes such that the connection from the outer bond pads to the plates of the electrode can be achieved from the end of the PZT elements. Also, isolation cuts 230 in the metallization of the PZT elements may prevent the opposite sides of the electrodes from shorting to each other.

In some embodiments, the ultrasound transducer elements 212, e.g., the PZT elements may be manufactured on a flexible substrate such as the flexible substrate 814. A single tablet of PZT would be formed with a continuous electrode connecting all 4 of the long surfaces. An isolation cut 230 would then be made parallel to the one long edge on one side and the other long edge on the opposite side. The PZT tablet would then be glued to the flexible substrate 814. In some examples, dicing the PZT tablet into 64 individual elements parallel to the tablet short edge would then provide an array that could be wrapped around the backing material 420 and held between the proximal and distal integrated circuit controllers 210 and 220. FIG. 6 shows an exploded illustration of the scanner assembly. In some examples, the number of PZT elements is between 32 and 128, for example, 64.

Figure 8B:
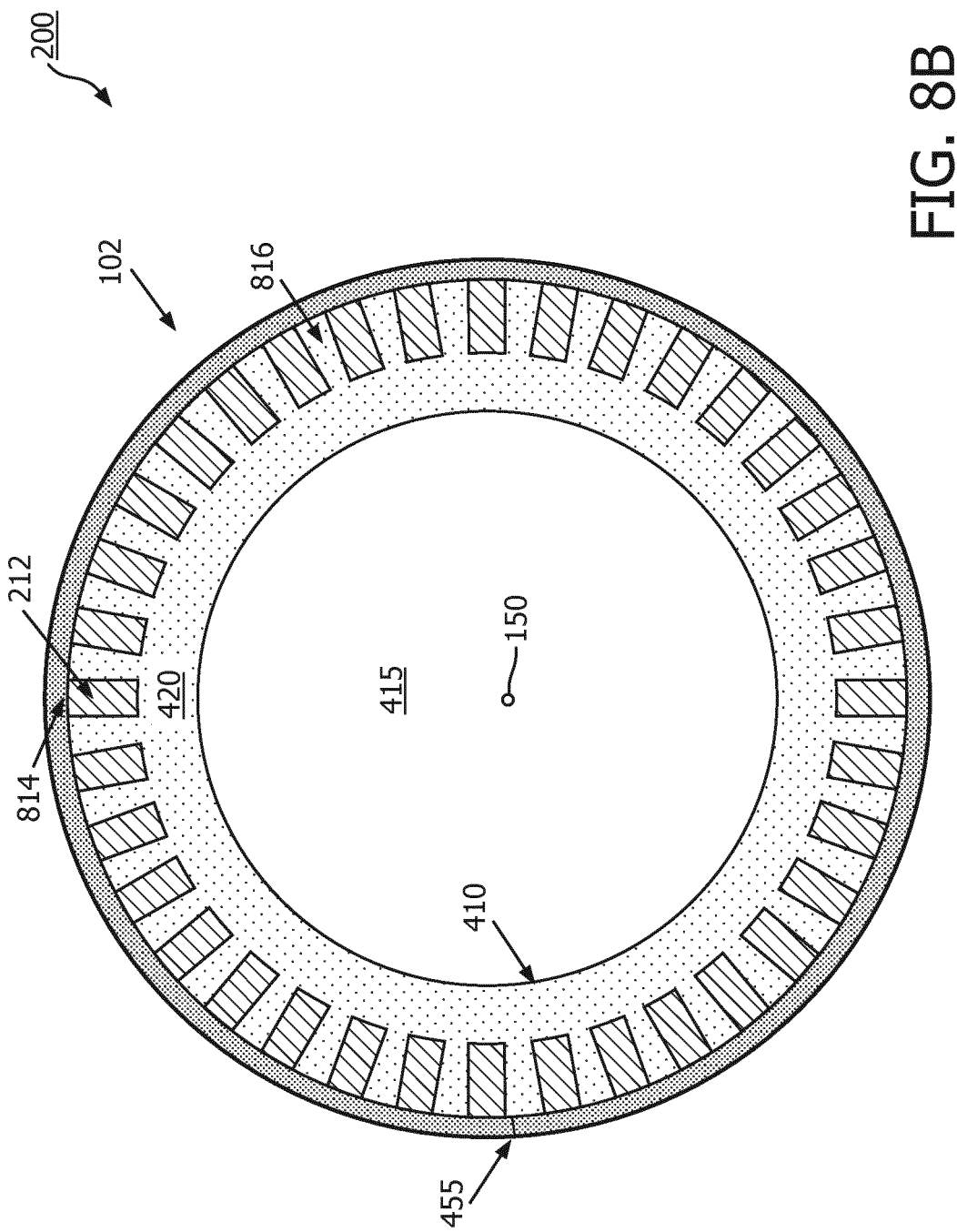
FIG. 8B is a diagrammatic cross-sectional view of an intraluminal imaging device along section line 8-8 of FIG. 7, according to aspects of the present disclosure.

FIG. 8B is a diagrammatic cross-sectional view of the intraluminal imaging device 102 along section line 8-8 of FIG. 7, according to aspects of the present disclosure. The cross-sectional view is shown along a plane extending through the imaging assembly 200 perpendicular and/or orthogonal to the longitudinal axis 150. The flexible substrate 814 is rolled around the longitudinal axis 150 of the flexible elongate member 122. The ultrasound transducer elements 212 are mounted on the flexible substrate 814. In some embodiments, as described with respect of FIG. 8A, the ultrasound transducer elements 212 are disposed, e.g., formed or mounted, on the flexible substrate 814, and the flexible substrate 814 is rolled around the longitudinal axis 150 such that relative to the ultrasound transducer elements 212, the flexible substrate 814 is farther away from the longitudinal axis 150 than the transducer elements 212. The ultrasound transducer elements 212 are configured to transmit acoustic waves away from the longitudinal axis 150. The ultrasound energy emitted by the elements 212 must thus pass through the material of the flexible substrate 814. In some examples, the flexible substrate 814 is an acoustic matching layer between the ultrasound transducer elements 212 and physiology within the patient, such as blood or tissue, acoustically coupled to the outer surface of the flexible substrate 814. The material of the flexible substrate 814 can be selected to optimize the transmission of ultrasonic energy. In some examples, the material of the flexible substrate 814 is selected to optimize flexibility so that the flexible substrate 814 can be rolled around the longitudinal axis 150.

After rolling the flexible substrate 814 around the longitudinal axis 150, an opening may exist along the butt joint 455 between the two edges of flexible substrate 814. This opening would allow fluid ingress. In some embodiments, a bead of material is provided on the edges to provide a seal along to joint 455 to connect the two edges of the rolled flexible substrate 814 to close the opening. The seal may prevent body fluid, such as blood from entering the imaging assembly 110.

As shown in FIG. 8B, the acoustic backing material 420 may be placed between the inner member 410 and the ultrasound transducer elements 212. The acoustic backing material 420 can also extend between the inner member 410 and the flexible substrate 814 such that the acoustic backing material 420 extends between the elements 212 within the space 816. The backing material 420 may prevent, e.g., dampen, acoustic waves such that ultrasonic energy advantageously only propagates away from the longitudinal axis 150. As shown, the inner member 410 creates the lumen 415 around the longitudinal axis 150. In some examples, the backing material 420 may extend to the flexible substrate 814 at the openings between the ultrasound transducer elements 212 and cover a space between the ultrasound transducer elements 212.

Figure 9:
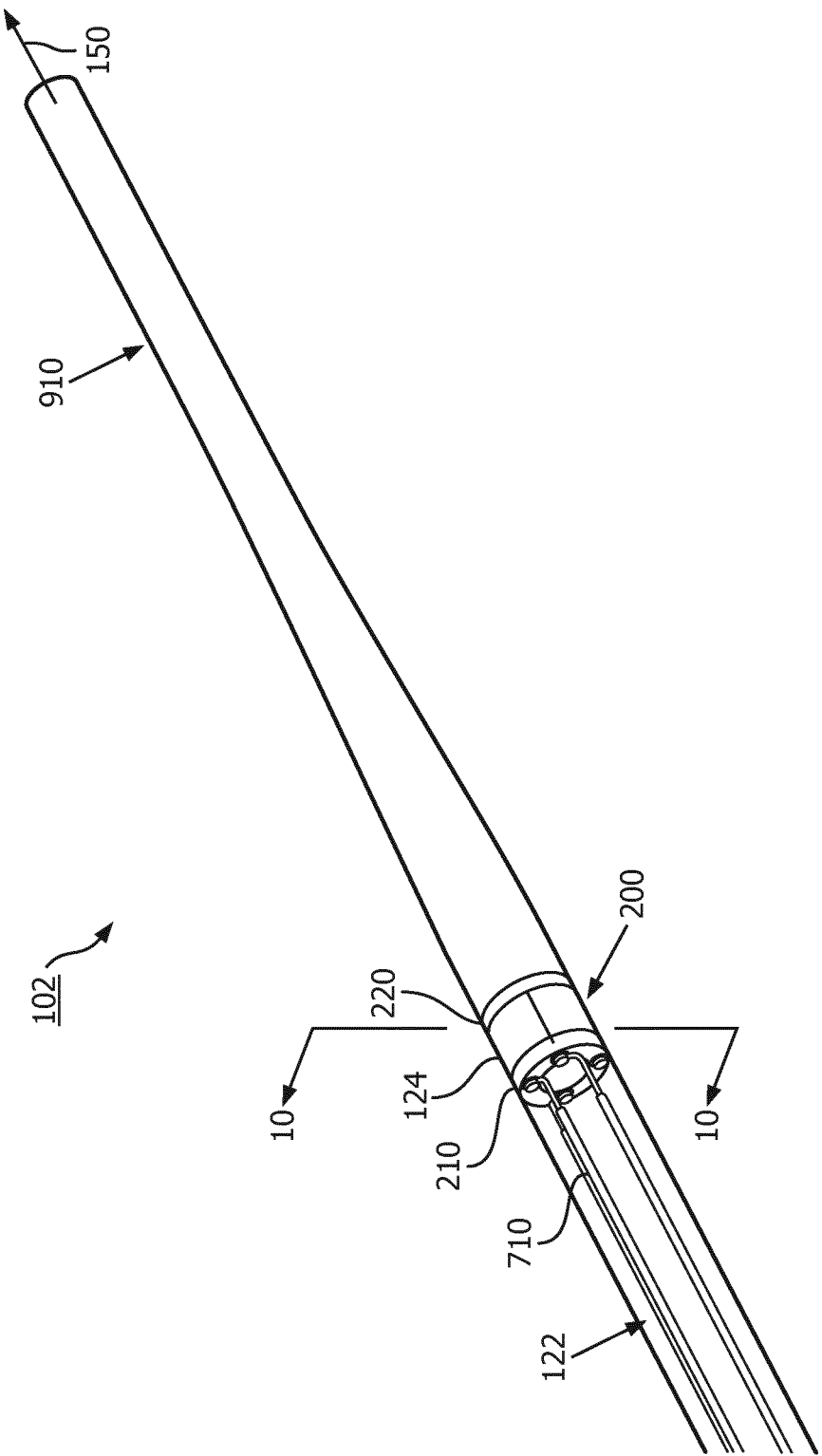
FIG. 9 is a diagrammatic isometric view of a distal portion of an intraluminal imaging device, according to aspects of the present disclosure.

FIG. 9 is a diagrammatic isometric view of a distal portion of the intraluminal imaging device 102, according to aspects of the present disclosure. The imaging assembly 200 is disposed at the distal portion of the flexible elongate member 122. A flexible distal member 910 extends distally from the imaging assembly 200. The distal member 910 can include a lumen in communication with the lumen 415 of the inner member and through which the guide wire 118 extends. The imaging assembly 200 includes the ultrasound transducer array 124 disposed between the annularly-shaped controllers 210, 220. Because of the relatively short stiff length associated with the imaging assembly 200, in some embodiments, the device 102 can include two or more imaging assemblies. For example, the imaging assemblies can be coupled to the flexible elongate member 122 and separated by a distance of between 2 mm and 10 mm. In such embodiments, multiple locations within a body lumen can be simultaneously. Different locations within the vessel can be imaged without moving the device 102.

Figure 10:
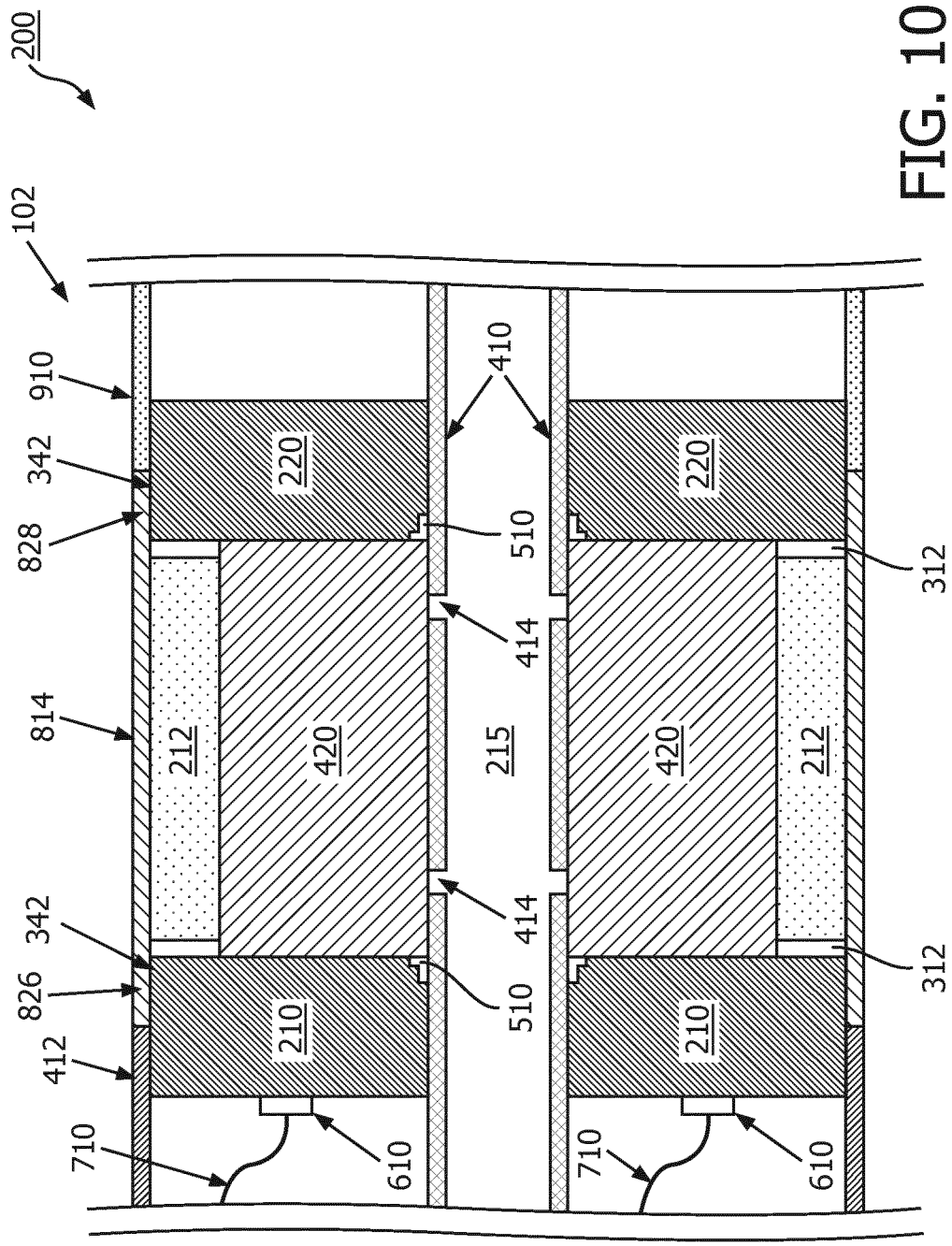
FIG. 10 is a diagrammatic cross-sectional view of the intraluminal imaging device along section line 10-10 of FIG. 9, according to aspects of the present disclosure.

FIG. 10 is a diagrammatic cross-sectional view of the intraluminal imaging device 102 along section line 10-10 of FIG. 9, according to aspects of the present disclosure. The imaging device 102 is illustrated along a plane parallel to or intersecting the longitudinal axis 150. In some examples, the cross-sectional view illustrated in FIG. 10 is perpendicular the cross-sectional view illustrated in FIG. 8B.

The transducer elements 212 are coupled to the flexible substrate 814 and extend longitudinally between the controllers 210, 220. Electrical communication between the controllers 210, 220 and the transducer elements 212 is established by contact with the bond pads 312 disposed along the outer diameter of the controllers 210, 220. The controllers 210, 220 are in electrical communication via conductive traces (e.g., conductive traces 430) disposed on the inner member 410. Bond pads 510 of the controllers 210, 220 are provided along the inner diameter and contact the conductive traces of the inner member 410. Bond pads 610 are disposed on a proximal surface of the controller 210 and are electrically and mechanically coupled to the conductors 710. The imaging assembly 200 is disposed at the distal portion of the flexible elongate member of the device 102, including the inner member 410 and the outer member 412. The inner member 410 extends through the lumens of the controllers 210, 220. The distal member 910 extends distally from the imaging assembly 200. In some embodiments, the outer member 412 forms a lap joint with the controller 210 and/or the distal member 910 forms a lap joint with the controller 220. The flexible substrate 814 can also form a lap joint with the controllers 210, 220. The backing material 420 extends in the space defined by the inner member 410, the controllers 210, 220, the flexible substrate 814, and/or the transducers 212. In some embodiments, the backing material 420 is liquid and is introduced into the space via recesses 414 in the inner member 410. The backing material 420 can harden and mechanically coupled the components of the imaging device 102. In some embodiments, adhesive is used between the various components of the imaging device 102 for mechanical coupling.

Figure 11:
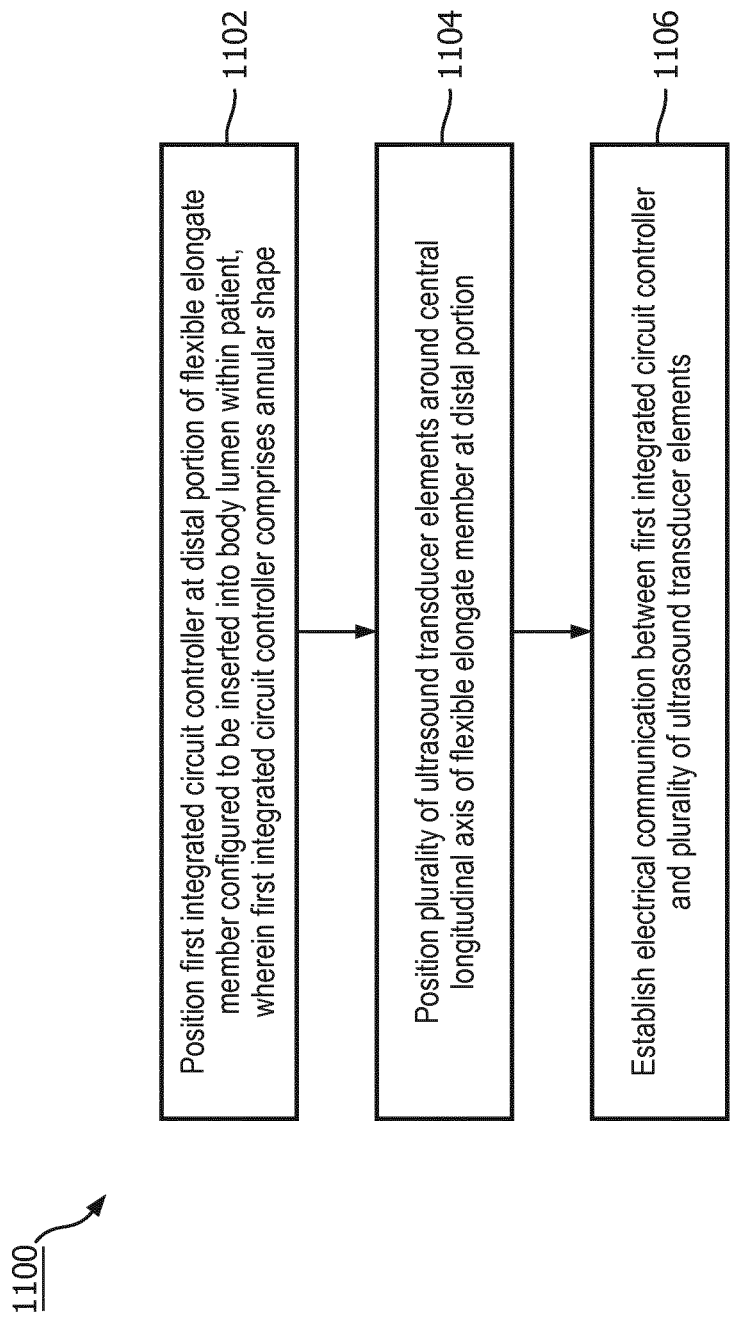
FIG. 11 is a flow diagram of a method of manufacturing an intraluminal imaging device, according to aspects of the disclosure.

FIG. 11 is a flow diagram of a method 1100 of assembling an intraluminal imaging device, including an imaging assembly as described herein. It is understood that the steps of method 1100 may be performed in a different order than shown in FIG. 11, additional steps can be provided before, during, and after the steps, and/or some of the steps described can be replaced or eliminated in other embodiments. The steps of the method 1100 can be carried out by a manufacturer of the intraluminal imaging device 102.

At step 1102, the method 1100 includes positioning a first integrated circuit controller at a distal portion of a flexible elongate member configured to be inserted into body lumen within patient. The first integrated circuit controller can comprises an annular shape. For example, as shown in FIG. 1, the imaging assembly 110 may be positioned at the distal portion of the flexible elongate member 122. In some embodiments and as shown in FIG. 1, the flexible elongate member 122 may be inserted into a body lumen such as the vessel 120 within a patient. In some examples, the imaging assembly 700 of FIG. 7 may be positioned at the distal portion of the flexible elongate member 122. In some embodiments, as shown in FIG. 7, the imaging assembly 700 may include a plurality of ultrasound transducer elements 212.

At step 1104, the method 1100 includes positioning a plurality of ultrasound transducer elements around longitudinal axis of flexible elongate member at distal portion. For example, the step 1104 can include arranging the plurality of ultrasound transducer elements around a longitudinal axis of the flexible elongate member. In some examples, as shown FIGS. 8A and 8B, the ultrasound transducer elements 212 may be disposed on a flexible substrate and the flexible substrate may be arranged around the longitudinal axis 150 of the flexible elongate member. For example, the imaging assembly 110 may be disposed at a distal portion of the flexible elongate member 122 such that imaging assembly 110 can be used to image the lumen when the distal portion of the flexible elongate member 122 is inserted into the patient vessel 120. In some examples, the plurality of ultrasound transducer elements 212 may be arranged in an annular configuration, such as in a circular configuration or a polygon configuration. In some examples, the ultrasound transducers 212 may be mounted to the flexible substrate.

At step 1106, the method 1100 includes establishing electrical communication between first integrated circuit controller and plurality of ultrasound transducer elements. In some embodiments, as shown in FIG. 2, the annularly shaped controllers 210 and 220 are coupled to the ultrasound transducers 212 and are in communication with the ultrasound transducers 212. As shown in FIGS. 3, 5 and 6, the annularly shaped controller 220 may include outer bond pads 312 and such that the ultrasound transducers 212 may couple and communicate to the controller 220 through the outer bond pads 312.

In some embodiments, the method 1100 may include positioning the ultrasound transducers 212 around a support member. For example, the ultrasound transducers 212 may be wrapped in a rolled or cylindrical configuration around an inner member 410 of FIGS. 4A and 4B. In some embodiments, as shown in FIGS. 5A, the method 1100 includes positioning a pre-formed backing material 420 between the ultrasound transducers 212 and the inner member 410. The backing material can be configured as a de-matching material to attenuate sound waves that are directed inwardly toward the longitudinal axis of the flexible elongate member. By attenuating these sound waves, acoustic energy is directed from the transducer elements outwardly away from the longitudinal axis to the physiology within the patient body. In some embodiments, the method 1100 includes arranging the inner member 410 along the longitudinal axis of the flexible elongate member. In some embodiments, the method 1100 includes extending a guide wire along the longitudinal axis 150 of the flexible elongate member within a lumen defined by the inner member 410. In some examples, the backing material 420 can provide structural support for the ultrasound transducer elements 212.

In some embodiments, as noted, the ultrasound transducer elements 212 may be disposed or formed on a flexible substrate 814 and the flexible substrate may be arranged around the longitudinal axis. The flexible substrate may act as an outer shell around the imaging assembly such that the outer shell contacts the plurality of ultrasound transducer elements and may perform as an acoustic matching layer around imaging assembly. In some embodiments, the method 1100 includes inserting, e.g., injecting, a filling material within a space 816 between adjacent ultrasound transducer elements and the flexible substrate 814 (e.g., the outer member). In some examples, the backing material may be inserted, e.g., injected between the inner member 410 and the ultrasound transducer elements 212 and then cured to provide a solid structure. In some embodiments, the method 1100 may further include etching a first and a second integrated circuit controller into an annular shape. In some examples, both the first and the second integrated circuit controller 210 and 220 may be in communication with the plurality of ultrasound transducer elements 212.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging device, comprising:
   a flexible elongate member defining a longitudinal axis and configured to be inserted into a body lumen within a patient;
   an imaging assembly disposed at a distal portion of the flexible elongate member, the imaging assembly comprising:
      a plurality of ultrasound transducer elements disposed around the longitudinal axis; and
      a first integrated circuit controller in communication with the plurality of ultrasound transducer elements,
   wherein the first integrated circuit controller comprises:
      an annular shape comprising:
         a diameter;
         a length in a longitudinal direction that is smaller than the diameter;
         a face extending along a portion of the diameter, wherein the face is oriented to face the plurality of ultrasound transducer elements; and
         an opening extending through the face;
      a plurality of first bond pads disposed on an outer portion of the face of the annular shape such that the plurality of first bond pads are oriented to face the plurality of ultrasound transducer elements; and
      a plurality of second bond pads disposed on an inner portion of the face of the annular shape around the opening.

2. The intraluminal imaging device of claim 1, further including:
   a second integrated circuit controller in communication with the ultrasound transducer elements and the first integrated circuit controller, wherein the second integrated circuit controller is annularly shaped.

3. The intraluminal imaging device of claim 2, wherein the imaging assembly further comprises a flexible substrate, wherein the plurality of ultrasound transducer elements is formed on the flexible substrate, wherein the flexible substrate extends longitudinally between the first and second integrated circuit controllers.

4. The intraluminal imaging device of claim 2, wherein the first integrated circuit controller is positioned proximally of the plurality of ultrasound transducer elements and the second integrated circuit controller is positioned distally of the plurality of ultrasound transducer elements.

5. The intraluminal imaging device of claim 4, wherein the flexible elongate member comprises an inner member extending through the opening of the first integrated circuit controller and an opening of the second integrated circuit controller, and
   wherein an acoustic backing material is disposed in a space defined by the inner member, the first and second integrated circuit controllers, and the plurality of ultrasound transducer elements.

6. The intraluminal imaging device of claim 4, wherein the flexible elongate member comprises an outer member and an inner member, wherein the inner member comprises a conductive trace, and wherein the first and second integrated circuit controllers are in electrical communication via the conductive trace of the inner member.

7. The intraluminal imaging device of claim 6, wherein the second integrated circuit controller includes an opening, and wherein the inner member of the flexible elongate member extends through the openings of the first and second integrated circuit controllers.

8. The intraluminal imaging device of claim 7, wherein a bond pad of the plurality of second bond pads is in contact with the conductive trace of the inner member.

9. The intraluminal imaging device of claim 1, wherein a quantity of the plurality of first bond pads equals a quantity of the plurality of ultrasound transducer elements.

10. The intraluminal imaging device of claim 1, wherein the first integrated circuit controller comprises a plurality of back bond pads coupled to a plurality of conductors extending along a length of the flexible elongate member.

11. The intraluminal imaging device of claim 1, wherein the length of the first integrated circuit controller in the longitudinal direction is 3 mm or less.

12. The intraluminal imaging device of claim 1, wherein the plurality of first bond pads are arranged to collectively form a further annular shape.

13. The intraluminal imaging device of claim 1, wherein the plurality of ultrasound transducer elements are directly adjacent to the first integrated circuit controller.

14. The intraluminal imaging device of claim 1, further comprising:
   a flexible substrate disposed around the longitudinal axis, wherein the plurality of ultrasound transducer elements is coupled to the flexible substrate; wherein the plurality of ultrasound transducer elements is disposed circumferentially around the longitudinal axis, and
   wherein the plurality of first bond pads is disposed circumferentially on the face of the first integrated circuit controller such that the plurality of first bond pads is positioned interior to the flexible substrate.

15. The intraluminal imaging device of claim 1, wherein each of the plurality of the first bond pads is in direct contact with one respective transducer element of the plurality of ultrasound transducer elements.

16. The intraluminal imaging device of claim 1, wherein the face of the annular shape is oriented perpendicular to the longitudinal axis.

17. The intraluminal imaging device of claim 1, wherein the plurality of first bond pads is electrically coupled to the plurality of ultrasound transducer elements, and wherein the plurality of second bond pads is not electrically coupled to the plurality of ultrasound transducer elements.

18. A method of assembling of an intraluminal imaging device, comprising:
   positioning a first integrated circuit controller at a distal portion of a flexible elongate member configured to be inserted into a body lumen within a patient, wherein the first integrated circuit controller comprises:
      an annular shape comprising:
         a diameter;
         a length in a longitudinal direction that is smaller than the diameter;
         a face extending along a portion of the diameter; and
         an opening extending through the face;
      a plurality of first bond pads disposed on an outer portion of the face of the annular shape; and
      a plurality of second bond pads disposed on an inner portion of the face of the annular shape;
   positioning a plurality of ultrasound transducer elements around a longitudinal axis of the flexible elongate member at the distal portion, wherein the face of the annular shape is oriented to face the plurality of ultrasound transducer elements such that the plurality of first bond pads are oriented to face the plurality of ultrasound transducer elements; and
   establishing electrical communication between the first integrated circuit controller and the plurality of ultrasound transducer elements.

19. The method of claim 18, further comprising:
   etching the first integrated circuit controller into the annular shape.

20. The method of claim 18, further comprising:
   positioning a second integrated circuit controller at the distal portion of the flexible elongate member, wherein the second integrated circuit controller comprises an annular shape.

21. The method of claim 20, wherein the plurality of ultrasound transducer elements is formed on a flexible substrate, and wherein the positioning a plurality of ultrasound transducer elements comprises:
   positioning the flexible substrate around a longitudinal axis of the flexible elongate member between the first and second integrated circuit controllers.

22. The method of claim 20, wherein:
   the positioning the first integrated circuit controller comprises extending an inner member of the flexible elongate member through the opening of the first integrated circuit controller; and
   the positioning the second integrated circuit controller comprises extending the inner member of the flexible elongate member through an opening of the second integrated circuit controller.

23. The method of claim 22, further comprising:
   establishing electrical communication between the first and second integrated circuit controllers, including contacting a bond pad of the plurality of second bond pads disposed on the first integrated circuit controller and a bond pad of the second integrated circuit controller to a conductive trace disposed on the inner member of the flexible elongate member.

* * * * *